United States Patent
Yokoi et al.

[11] Patent Number: 5,921,232
[45] Date of Patent: Jul. 13, 1999

[54] HANDY TYPE INHALER

[75] Inventors: Hiroyuki Yokoi; Masae Shibasaki, both of Saitama, Japan

[73] Assignee: A & D Company Limited, Tokyo, Japan

[21] Appl. No.: 08/793,095

[22] PCT Filed: Jul. 12, 1995

[86] PCT No.: PCT/JP95/01383

§ 371 Date: Apr. 16, 1997

§ 102(e) Date: Apr. 16, 1997

[51] Int. Cl.$^6$ .................................................. A61M 11/00
[52] U.S. Cl. .............................. 128/200.14; 128/200.16; 128/203.12
[58] Field of Search ......................... 128/200.14, 200.16, 128/200.17, 203.15, 200.18, 203.12

[56] References Cited

U.S. PATENT DOCUMENTS

| | | | |
|---|---|---|---|
| 2,266,705 | 12/1941 | Fox et al. ............................. | 128/202.22 |
| 5,363,842 | 11/1994 | Mishelevich et al. ............. | 128/200.14 |
| 5,419,315 | 5/1995 | Rubsamen ........................... | 128/200.14 |
| 5,511,539 | 4/1996 | Lien .................................... | 128/200.14 |
| 5,551,416 | 9/1996 | Stimpson et al. ................... | 128/200.14 |

FOREIGN PATENT DOCUMENTS

| | | |
|---|---|---|
| 57-51541 | 9/1980 | Japan . |
| 61-109545 | 7/1986 | Japan . |
| 475750 | 7/1992 | Japan . |
| 3000139 | 5/1994 | Japan . |
| 722747 | 4/1995 | Japan . |

*Primary Examiner*—Aaron J. Lewis
*Attorney, Agent, or Firm*—Sixbey Friedman Leedom & Ferguson; Thomas W. Cole

[57] ABSTRACT

The inhaler has a medicine atomizing means 10, a nozzle 12 for discharging medicine atomized by said medicine atomizing means 10, and a gripping casing 14. Said casing 14 has a small-diametered cylindrical section 14a, a large-diametered cylindrical section 14b, and a bottom 14c, and is formed so as to have a bottom with its upper end side open. Furthermore, the same has a roughly gourd-shaped cross-section which connects said small-diametered cylindrical section 14a and said large-diametered cylindrical section 14b at the side thereof. Said medicine atomizing means 10 is incorporated in the large-diametered cylindrical section 14b side of the casing 14, and has a piezoelectric vibrator 10a and a vibration liquid. Said nozzle 12 is composed of a transparent rubber-based member and is attached in such a manner that the base part side is fitted to the first annular protrusion 46e of the cover 46, whereby it is possible to optionally change the discharging direction of medicine by changing the fitting state of the base part.

2 Claims, 4 Drawing Sheets

HANDY TYPE INHALER

FIELD OF THE INVENTION

The present invention relates to a handy type inhaler and in particular relates to a technology for improving the convenience in use thereof.

BACKGROUND OF THE INVENTION

An inhaler has been already known as an instrument used for treating the nose and throat, and this kind of an inhaler is, for example, utilized for treating primary catarrh, allergic rhinitis, etc. An inhaler used for such a therapy is such that heat or vibration is given to medicine in order to atomize the same and a patient is caused to inhale the same. A handy type and an installation type are available on the market.

Furthermore, various kinds of handy type inhalers are proposed in view of their portability, for example, several structural examples are disclosed in Japanese laid-open utility model publications Nos. 51541 of 1983, 109545 of 1986, 75750 of 1990, etc. An inhaler disclosed in Japanese laid-open utility model publication No. 51541 of 1983 is provided with a cylindrical casing in which an inhaler is incorporated, and the casing is such that the cross-section thereof connects a small-diametered semicircle with a large-diametered semicircle and is made cylindrical, and a nozzle which is able to discharge atomized medicine is provided in a fixed state at the small-diametered semicircle at the upper side of the casing.

With an inhaler having such a structure, when using the same, the large-diametered semicircle section of the casing is gripped by a hand and the nozzle secured at the small-diametered semicircle is caused to face the nose or throat. Furthermore, an inhaler disclosed by Japanese laid-open utility model publication No. 109545 of 1986 is provided with a casing formed to be roughly box-like, in which an inhaler is incorporated, and the width of the casing is made tapered from the rear end thereof toward the front end side, and a nozzle which is able to discharge atomized medicine is provided in a fixed state at the front end side.

With the inhaler having such a structure, when using the same, the rear end side is gripped by a hand and the nozzle at the front end side, which is made tapered, is caused to face the nose or throat. Furthermore, an inhaler disclosed by Japanese laid-open utility model publication No. 75750 of 1990 is provided with a cylindrical casing in which an atomizing means is incorporated, and a nozzle which is able to discharge atomized medicine is fixed at the upper side of the casing.

With an inhaler having such a structure, when using the same, the cylindrical casing is gripped by a hand and is caused to face the nose or throat. However, in such conventional inhalers, there still remain technical themes to be described below.

That is, in the abovementioned utility model publications, since the nozzle is fixed in both of them, the inhalers are used while gripping the large-diametered semicircle section, the rear end section of the casing, or the cylindrical casing. However, this kind of atomizer is used by not only an adult but also a child. With such a structure of an atomizer disclosed in the abovementioned publications, if the large-diametered semicircle side section, the rear end portion of the casing or the gripping section consisting of a cylindrical casing is set to a size suitable for an adult, the same is too large for use by a child, and it is difficult for a child to grip. To the contrary, if the gripping section is set to a size suitable for a child, the size is not suitable for an adult, and it is difficult for an adult to use. Therefore, there is some parts thereof to be further improved for the convenience in use.

The present invention was developed in view of solving the abovementioned problems, and it is therefore an object of the invention to provide an improved handy type inhaler which is easily adaptable for the use by not only an adult but also a child.

DISCLOSURE OF THE INVENTION

In order to achieve the above object, the invention is characterized in that the same provides a handy type inhaler consisting of a medicine atomizing means and a nozzle for discharging medicine atomized by said medicine atomizing means and further has a cylindrically gripping casing in which said atomizing means is incorporated, wherein said gripping casing has a roughly gourd-shaped cross-section which connects a small-diametered cylindrical section with a large-diametered cylindrical section at the sides thereof and said nozzle is attached to the upper end side of said casing so that the discharging direction of the atomized medicine can be changed.

An operating switch of said medicine atomizing means may be provided at the part at which said small-diametered cylindrical section of the gripping casing is connected to said large-diametered cylindrical section thereof. Furthermore, an indication lamp may be adopted adjacent to said operating switch at the gripping casing.

With a handy type inhaler constructed as described above, since the gripping casing has a roughly gourd-shaped cross-section which connects the small-diametered cylindrical section with the large-diametered cylindrical section at the sides thereof, an adult is able to grip the large-diametered cylindrical section side and a child is able to grip the small-diametered cylindrical section side. At this time, since the nozzle is mounted at the upper end side of the casing so that the discharging direction of the atomized medicine can be changed, it is possible to change the discharging direction of the atomized medicine according to a gripped state.

According to the construction defined in claim 2, since an operating switch of an atomizing means is provided at the connection part where the small-diametered cylindrical section is linked with the large-diametered cylindrical section, it is possible to operate the switch with finger tips with the casing gripped. According to the construction defined in claim 3, since an indication lamp is secured adjacent to the operating switch, it is possible to immediately check the switch operation.

PREFERRED EMBODIMENT OF THE INVENTION

Figure 1:
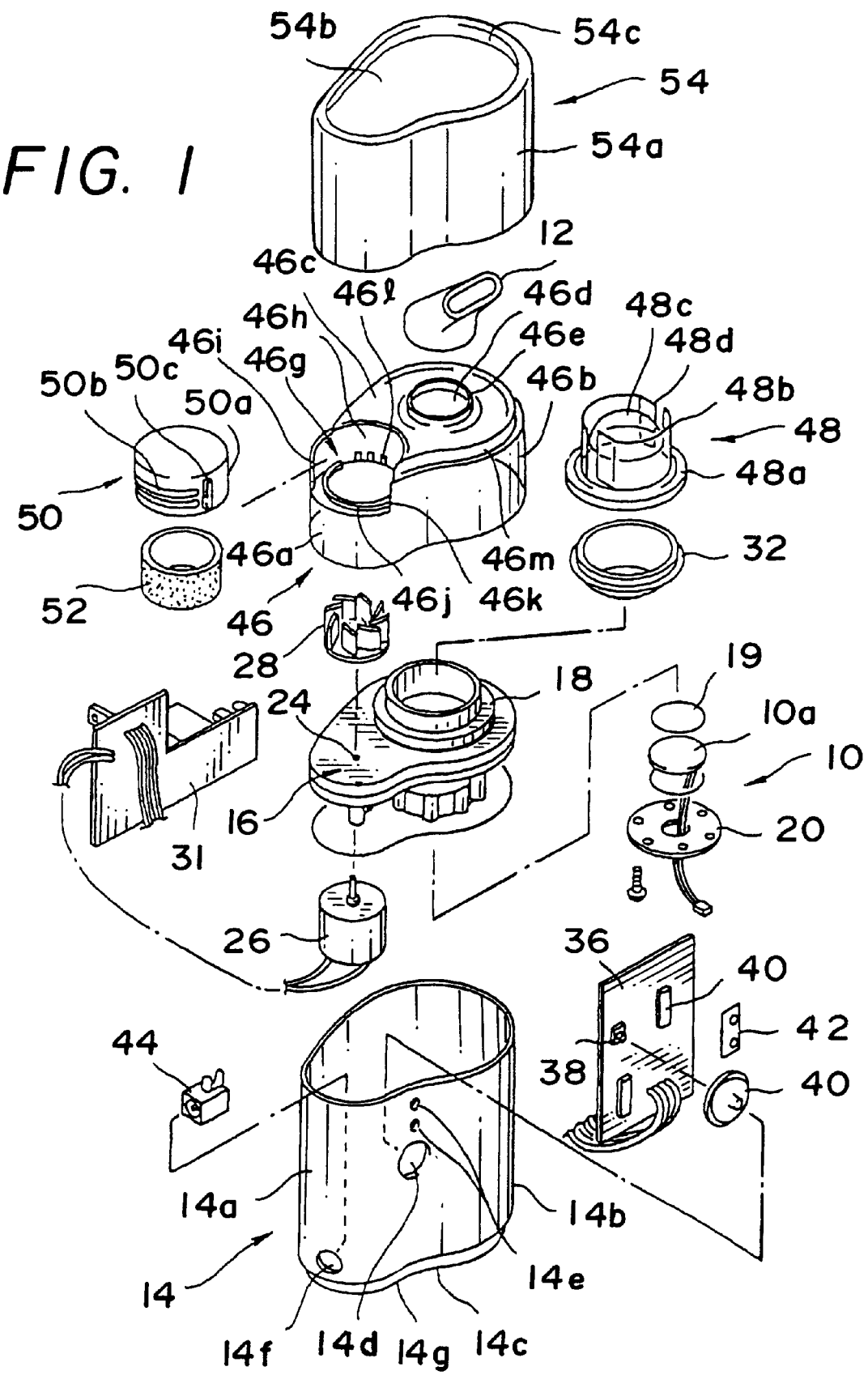
FIG. 1 is a disassembled perspective view showing one preferred embodiment of a handy type inhaler according to the invention.
Figure 2:
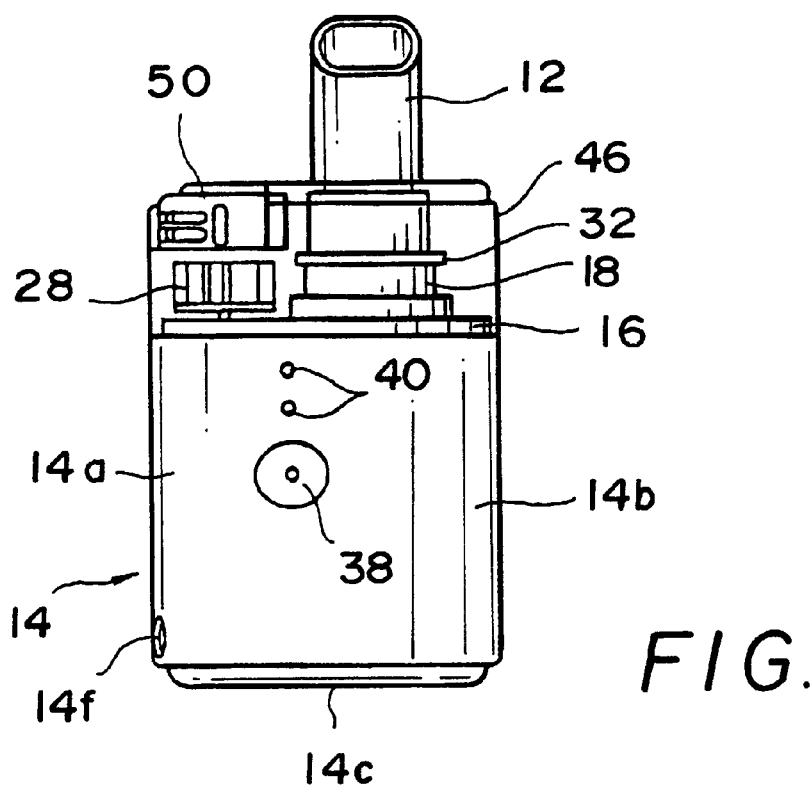
FIG. 2 is the front elevational view showing an assembled inhaler in FIG. 1 with its cap removed.
Figure 3:
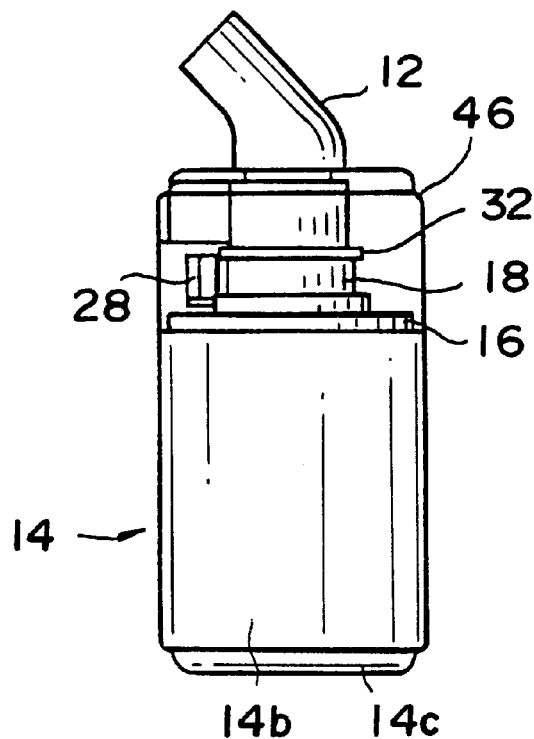
FIG. 3 is the right side elevational view of FIG. 2.
Figure 4:
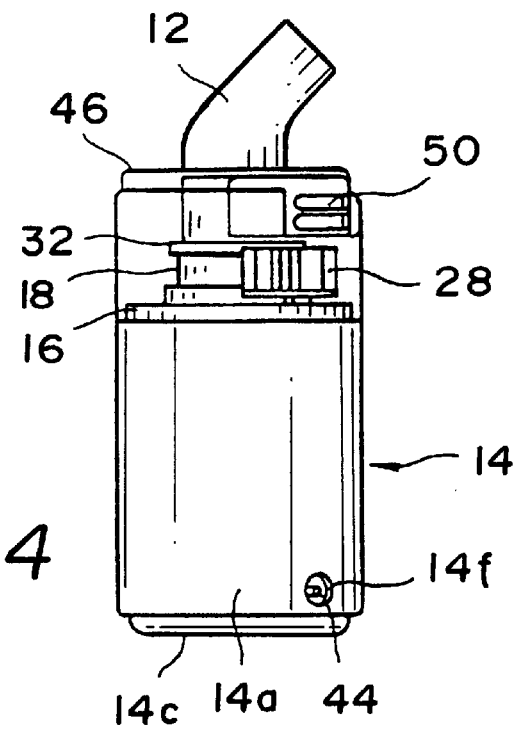
FIG. 4 is the left side elevational view of FIG. 2.
Figure 5:
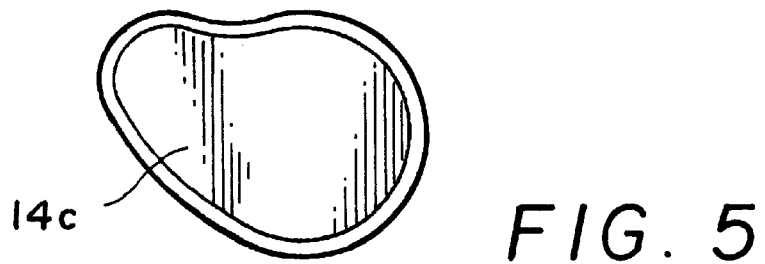
FIG. 5 is the bottom view of FIG. 2.
Figure 6:
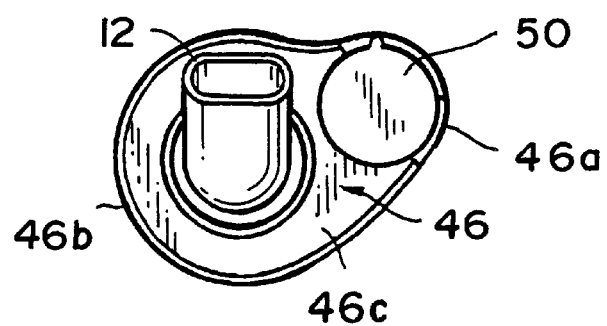
FIG. 6 is the plan showing the top section of FIG. 2.
Figure 7:
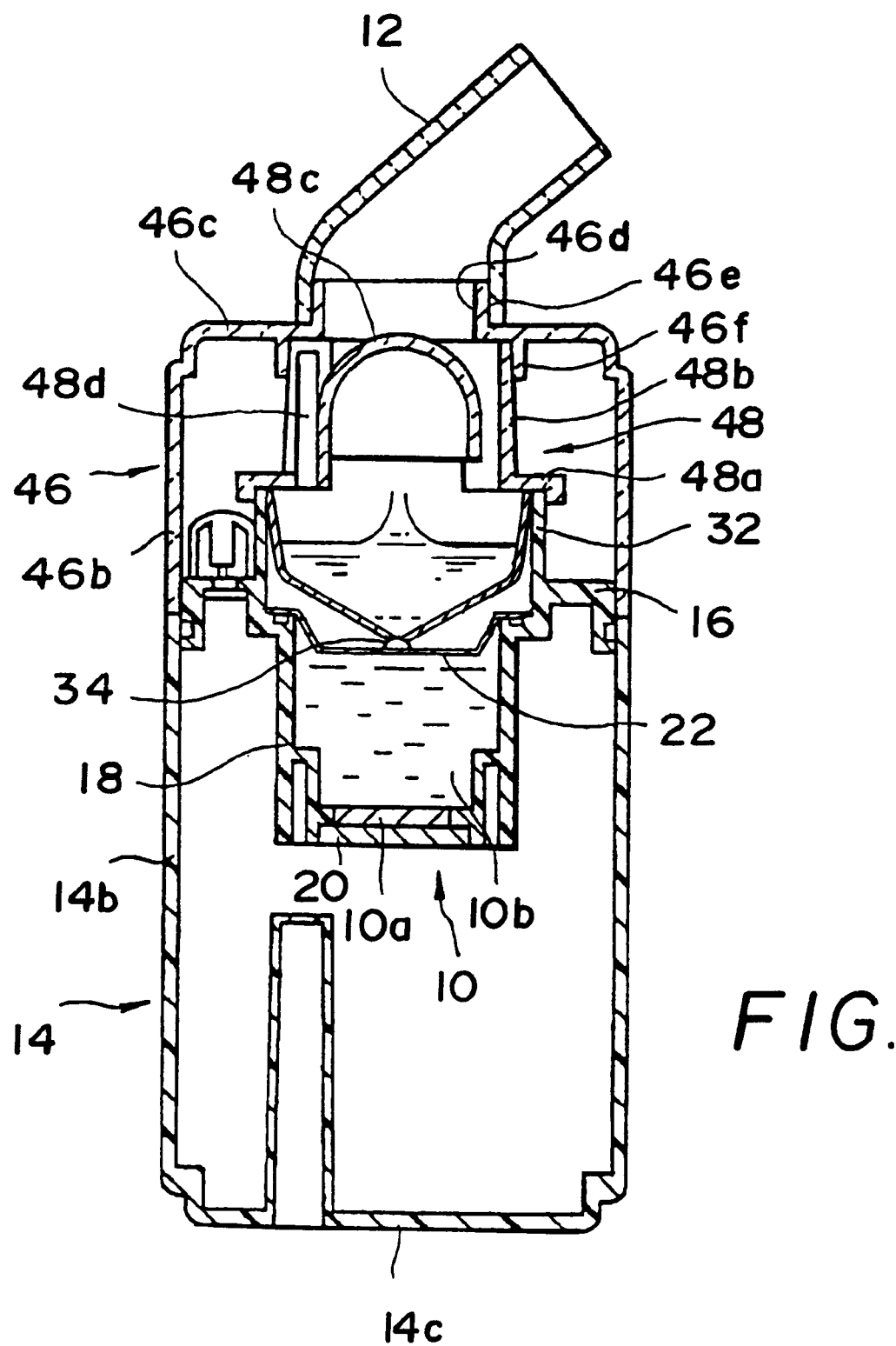
FIG. 7 is a cross-sectional view showing major parts of FIG. 2.

A detailed description will be given of a preferred embodiment of the invention with reference to the drawings attached herewith. FIG. 1 through FIG. 6 show a preferred embodiment of a handy type inhaler according to the invention. An inhaler shown in these drawings has a medicine atomizing means 10, a nozzle 12 for discharging the medicine atomized by said medicine atomizing means, and a gripping casing 14. Said casing 14 has a small-diametered cylindrical section 14*a*, a large-diametered cylindrical section 14*b*, and a bottom section 14*c* and is formed so as to have a bottom with the upper end thereof open. Furthermore, the same has a roughly gourd-shaped cross-section which connects the small-diametered cylindrical section 14*a* with the large-diametered cylindrical section 14*b* at the sides thereof.

Said medicine atomizing means 10 is incorporated in the large-diametered cylindrical section 14*b* in the casing 14 and has a piezoelectric vibrator 10*a* and a vibration liquid 10*b*. Said piezoelectric vibrator 10*a* is fixed at the lower end of a hollow cylindrical body 18 supported at a cover plate 16 which closes the open end of said casing 14 via a protection sheet 19 and an attaching plate 20 so that said hollow cylindrical body 18 is closed. Said vibration liquid may be distilled water and is sealed in said hollow cylindrical body 18 by adhering a film-like sheet 22 to the intermediate part of the hollow cylindrical body 18 so that the vibration liquid is brought into contact with the protection sheet 19 provided at the upper surface of the piezoelectric vibrator 10*a*.

Said hollow cylindrical body 18 is fixed at one end side of said cover plate 16 (the large-diametered cylindrical section 14*b* side of the casing 14) which is formed to be gourd-shaped, so that the upper end thereof protrudes upward, and a through-hole 24 is formed at the other end of the cover plate 16 (the small-diametered cylindrical section 14*a* side of the casing 14). The rotating axis of a motor 26 is inserted from below into the through-hole 24, and an impeller 28 is fitted from above to the rotating axis thus inserted.

The motor 26 and impeller 28 have diameters which are smaller than the inner circumferential diameter of the small-diametered cylindrical section 14*a* of the casing 14, and create an air flow which sends out the atomized medicine toward the nozzle 12 side. Power is supplied to the motor 26 via a control circuit mounted on a substrate 31. Furthermore, in this preferred embodiment, power for driving a piezoelectric element 10*a* and motor 26 is supplied by a secondary battery incorporated in the casing 14, the illustration of which is omitted herein.

A medicine disk 32 which is able to accommodate medicine is fitted to the inner side of the part where the hollow cylindrical body 18 protrudes upward of the cover plate 16. A medicine disk 32 of this preferred embodiment is concretely shown in FIG. 7, and the medicine disk 32 has a bottom inclined downward and a gelled substance 34 intervenes between the bottom and the film-shaped sheet 22. This gelled substance 34 is able to increase the atomizing efficiency of medicine by improving the transmission of vibrations and consists of a polymer, a dampening agent, water, a preserving agent, a surface-active agent, etc.

On the other hand, one large-diametered through-hole 14*d* is formed at the front side of the casing 14, and two small-diametered through-holes 14*e* are formed at the upper side thereof. Furthermore, one circular through-hole 14*f* is formed at the lower end of the side of the small-diametered cylindrical section 14*a* of the casing 14. An operation switch 38 supported at a substrate 36 which is inserted into the rear side of the large-diametered through-hole 14*d* is inserted into the large-diametered through-hole 14*d*, and a switch cover 40 is attached to the inserted operation switch.

An indication lamp 40 supported at the substrate 36 is disposed at the rear side of the small-diametered through hole 14*e*, and said indication lamp 40 is composed of two light emitting diodes, wherein the two light emitting diodes are provided so that they face the small-diametered through-hole 14*e* via a cover 42. Furthermore, one of the two light emitting diodes blinks corresponding to turning on and off of the operation switch 38 and the other is lit when charging a secondary battery.

A connector 44 connected to the secondary battery is attached to the rear side of the circular through-hole 14*f*, and an adapter 88 connected to a commercial power source is inserted into this connector 44 when charging the secondary battery. With the above construction, the operation switch 38 is disposed at the position where the small-diametered cylindrical section 14*a* of the casing 14 is connected to the large-diametered cylindrical section 14*b* thereof, and the indication lamp 40 is provided in the vicinity of this operation switch 38.

The cover member 16 is fitted to and fixed at the upper opening end of the casing 14 so that a part of the upper side thereof protrudes therefrom, and a transparent cover 46 is attached from above to the protruded part. The cover 46 is formed so as to have an open lower end and the cross-section thereof is formed to be gourd-shaped as in the casing 14. Furthermore, the cover 46 has a small-diametered circumferential wall 46*a* and a large-diametered circumferential wall 46*b* respectively having diameters corresponding to that of the small- and large-diametered cylindrical sections 14*a* and 14*b*, and a ceiling part 46*c*.

A circular through-hole 46*d* which is caused to pass through the ceiling on the center of the large-diametered circumferential wall part 46*b* is formed at the center thereof, and a first annular protrusion 46*e* protruding upward is provided at the surrounding of the circular through-hole 46*d*, and at the same time a second annular protrusion 46*f* protruding downward is provided outside the first annular protrusion 46*e*.

Furthermore, a circular through-hole 46*g* is formed in the center of the small-diametered circumferential wall part 46*a*, and an arcuate wall 46*h* connected to the small-diametered circumferential wall part 46*a* is formed at the inner circumferential side of said circular through-hole 46*g*, and an arcuate notched part 46*i* is formed at the small-diametered circumferential wall part 46*a* at the position corresponding to said arcuate wall 46*h*. Furthermore, an arcuate projection part 46*j* protruding inwardly is formed at the inner circumferential face of the small-diametered circumferential wall part 46 at a height position where said notched part 46*i* is provided, and an arcuate projection 46*k* is integrally on the upper surface of said projection part 46*j*.

Still furthermore, a plurality of notched grooves 461 are formed at the inner circumferential face of said arcuate wall 46*h* at an appropriate interval along the circumferential direction. A rectifying member 48 of atomized medicine is mounted from below at the second annular protrusion 46*f* secured at the outer circumference of the circular through-hole 46*d*. Said rectifying member 48 is secured at the inner circumference of a flange part 48*a* integrally with said flange part 48 fitted to the upper end side of said hollow cylindrical body 18. The upper end side of said rectifying member 48 is composed of a hollow cylindrical part 48*b* fitted to the second annular protrusion 46*f* with both the ends open, a dome section 48*c* fixed at the inner circumferential face of said hollow cylindrical part 48*b* and a pair of slit holes 48*d* provided at the part opposite the hollow cylindrical part 48*b*.

With the rectifying member 48 thus constructed, the medicine atomized from the medicine disk 32 is caused to move upward and is brought into collision with the dome portion 48c, and the liquefied medicine brought into collision with the spherical inner surface of the dome portion 48c is thereafter reflected toward the center of the dome portion 48c and is mixed with the atomized medicine which is gradually caused to go up, in the dome portion 48c. Thereafter, the mixed medicine is sent out to the nozzle 12 side together with an air flow introduced via the slits 48d and created by the impeller 28 between the inner circumferential face of the hollow cylindrical portion 48*b* and the outer circumferential portion of the dome 48*c* so as to bypass at the lower end of the dome portion 48*c*.

An air flow regulating member 50 is attached in the opening portion 46*g*. Said air flow regulating member 50 is formed to be cap-like. A filter 52 is disposed on the inner circumferential face of the circumferential wall 50*a* thereof, and at the same time, a hole 50*b* extending in the circumferential direction and a slide grip 50*c* are provided at the circumferential wall 50*a*, and at the same time, a small-diametered protrusion 50*d* protruding upward is provided at the center of the ceiling part. This air flow regulating member 50 is positioned and mounted at the cover 46 so that the lower end inner circumference of the circumferential wall 50*a* is fitted to the arcuate protrusion 46*k*, and by causing the air flow regulating member 50*c* to move in the circumferential direction with said slide grip 50*c*, the hole 50*b* changes the length of a portion which is exposed to the notched part 46*i*, whereby the air flow created by the impeller 28 is regulated.

Furthermore, in such an adjusted state, a protrusion (not illustrated) is provided at the outer face of the circumferential wall 50*a* of the air flow regulating member 50, the mutual positional relationship between the hole 50*b* and the notched part 46*i* is fixed by gradually inserting this protrusion into the notched grooves 46*l*. The nozzle 12 is composed of a transparent rubber-based member in this preferred embodiment, and the base part thereof is mounted by fitting the same to the first annular protrusion 46*e*.

At this time, it is possible to optionally choose the discharging direction of the atomized medicine by changing the fitting state of the base part. Furthermore, in the case of this preferred embodiment, since the nozzle 12 is composed of a soft rubber based member, it is also possible to change the discharging direction by rotating the nozzle 12 in a state where the same is fitted to the first annular protrusion 46*e*. A cut-off part 46*m* which is able to be fitted to a cap 54 attached from above the cover 46 is formed at the outer circumferential edge of the ceiling part 4*c* of the cover 46. Said cap 54 has a circumferential part 54*a* and a ceiling part 54*b* of which the cross-section is similar to the cross-section of the casing 14.

A concave part 54*c* which is able to be fitted to a roughly gourd-shaped protrusion part 14*g* secured at the lower end face of the casing 14 is formed on the upper side of the ceiling part 54*b*. With a handy type inhaler constructed as described above, by turning on the operating switch 38 with medicine placed on the medicine disk 32, vibration of the piezoelectric vibrator is transmitted to the medicine via a vibration liquid 10*b*, whereby the medicine is atomized, and the atomized medicine is discharged through the nozzle 12 along with an air flow created by the impeller 28.

At this time, in an inhaler according to the preferred embodiment, since the gripping casing 14 has a roughly gourd-shaped cross-section which connects a small-diametered cylindrical part 14*a* with a large-diametered cylindrical part 14*b* at the sides thereof, an adult is able to grip the large-diametered cylindrical part 14*b* side, and a child is able to grip the small-diametered cylindrical part 14*a* side. Accordingly, since the nozzle 12 is attached to the upper end face side of the casing 14 so as to enable a changing of the discharging direction of the atomized medicine, it is possible to change the discharging direction of the atomized medicine according to the gripping state, whereby the convenience in use will be remarkably improved.

In this case, as shown in FIG. 1, the side to which the operating switch 38 is attached is made the front side and the large-diametered cylindrical part 14*b* is disposed at the right side thereof since, in this kind of inhaler, the majority of the users are right-handed people. However, in this preferred embodiment, since it is possible to easily change the direction of the nozzle 12 even though a left-handed man grips this large-diametered cylindrical part 14*b*, the inconvenience resulting from the use being restricted to either left or right hand can be eliminated.

Furthermore, with the conventional inhaler described above, if the nozzle is caused to face the nose or throat with the inhaler gripped by one arm since the direction of the nozzle is fixed, the inhaler must be gripped so as to turn the arm behind the inhaler, whereby a remarkably unnatural posture will be forced. With the inhaler according to the preferred embodiment, since it is possible to optionally choose the discharging direction of the atomized medicine from the nozzle 12, it is possible to avoid the use in an unnatural state.

Furthermore, since the gripping casing 14 is provided with an operating switch 38 for an atomizing means at the part which connects the small-diametered cylindrical section 14*a* with the large-diametered cylindrical part 14*b*, it is possible to operate the operating switch 38 with finger tips with the casing gripped. Furthermore, since the gripping casing 14 is provided with an indication lamp 40 adjacent to the operating switch 38, it is possible to immediately check the operation of the switch 38.

Still furthermore, although in the above preferred embodiment, a type composed of a piezoelectric vibrator 10*a* and a sealed vibration liquid 10*b* is illustrated as a medicine atomizing means 10, the invention is not limited to this type, for example the atomizing means may be a heating means such as a heater.

Industrial feasibility

As concretely described in the above preferred embodiment, a handy type inhaler according to the present invention is able to be used in a wide range from an adult to a child.

What is claimed is:

1. An inhaler having a medicine atomizing means and a nozzle through which medicine atomized by said medicine atomizing means is able to be discharged; and further having a gripping casing in which said medicine atomizing means is incorporated wherein said gripping casing is substantially gourd-shaped in cross-section in which a small-diametered cylindrical section having an axis of rotation and a large-diametered cylindrical section having an axis of rotation are connected at sides thereof such that said axes of rotation are parallel and spaced apart from one another, said large diametered cylindrical section configured for gripping by an adult and said small diametered cylindrical section configured for gripping by a child, wherein said medicine atomizing nozzle is movably attached to an upper end side of said casing so as to vary a discharging direction of atomized medicine, wherein said gripping casing is provided with an operating switch of said medicine atomizing means where said small-diametered cylindrical section and the large-diametered cylindrical section are connected thereby enabling either an adult or a child to operate the operating switch using fingertips.

2. An inhaler as set forth in claim 1, wherein said gripping casing is provided with an indication lamp adjacent to said operating switch.

* * * * *